US00PP08022P

United States Patent [19]

Wilhelm

[11] Patent Number: Plant 8,022

[45] Date of Patent: Nov. 3, 1992

[54] HYBRID RASPBERRY CV. "LAWRENCE"

[75] Inventor: Stephen Wilhelm, Oakland, Calif.

[73] Assignee: Sweetbriar Development Inc., Watsonville, Calif.

[21] Appl. No.: 713,952

[22] Filed: Jun. 11, 1991

[51] Int. Cl.[5] ..... A01H 5/00

[52] U.S. Cl. ..... Plt./46.2

[58] Field of Search ..... Plt./46.2

*Primary Examiner*—James R. Feyrer

*Attorney, Agent, or Firm*—Synnestvedt & Lechner

[57] ABSTRACT

The invention concerns a new and distinct variety of hybrid raspberry, the variety being particularly characterized and distinguished its significant primocane production from Aug. 15 to Nov. 30 accounting for one third of the total yield; the floricane production occurs from about May 7 to July 30; the fruit is of medium to large size, firm, and has drupelets of uniform size and color. The torus is short and tapering without prominent spicules. Fruit is of excellent fresh market quality with only a slight tendency to darken after harvest. The new variety holds its distinguishing characteristics through succeeding propagations by planting dormant canes, dormant root cuttings and non-dormant root shoot cuttings.

6 Drawing Sheets

This invention relates to a new variety of hybrid raspberry cv. "Lawrence" that was discovered and asexually reproduced by Stephen Wilhelm. It has as its seed parent "Sweetbriar" (U.S. Plant Pat. No. 4,486) and as its pollen parent Reiter 239 (unpatented).

The new raspberry cv. "Lawrence" is particularly distinguishable from other commercialized raspberry cultivars by the following combination of characteristics: its significant primocane production from August 15 to November 30 accounting for one third of the total yield; the floricane production occurs from about May 7 to July 30; the fruit is of medium to large size, firm, and has drupelets of uniform size and color. The torus is short and tapering without prominent spicules. Fruit is of excellent fresh market quality with only a slight tendency to darken after harvest.

The new variety holds its distinguishing characteristics through succeeding propagations by planting dormant canes, dormant root cuttings and non-dormant root shoot cuttings.

The new "Lawrence" raspberry cultivar may be distinguished from its pollen parent Reiter 239 by the following combination of characteristics:

The new variety is taller or more vigorous in growth and has darker colored leaves. Fruit of the new variety is larger, darker in color and not as bright.

The new "Lawrence" raspberry cultivar may be distinguished from its seed parent cv. "Sweetbriar" (U.S. Plant Pat. No. 4,486) by the following combination of characteristics:

The new variety is taller or more vigorous. It forms less lateral branches, and its leaves are less cupped. The new variety is more resistant to powdery mildew and has a lower winter cold requirement.

Fruit of the new variety is more symmetrical in shape and uniform in druplet arrangement. Fruit is as much as 2 weeks earlier in the spring. Harvest from primocanes begins two weeks later and peaks 2–3 weeks later in the fall.

In the accompanying drawings FIG. 1 illustrates the new raspberry variety cv. "Lawrence" in color as grown in Watsonville, Calif. and shows various stages of fruit development. FIG. 2 shows a mature leaf and various stages of flower development.

Figure 1:
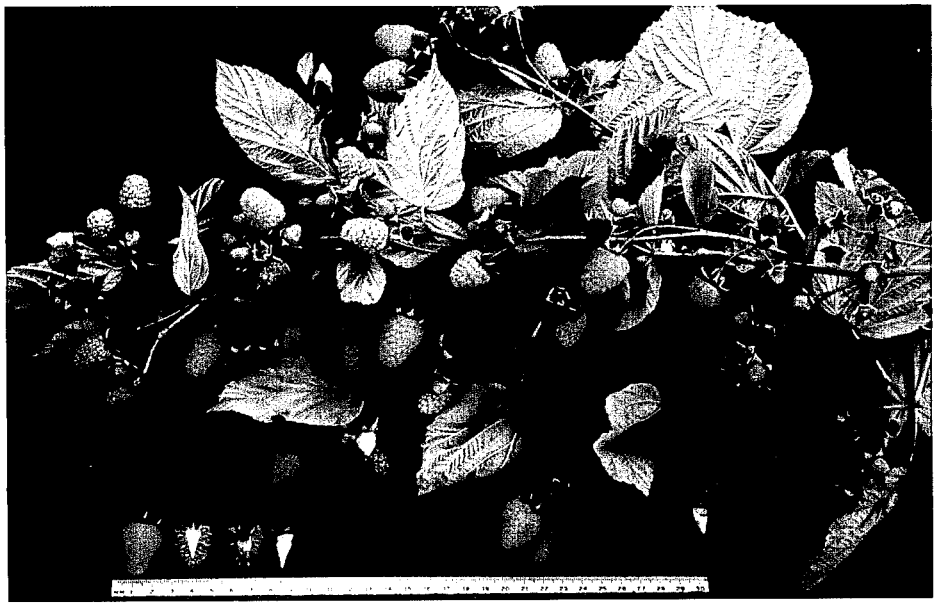
Figure 2:
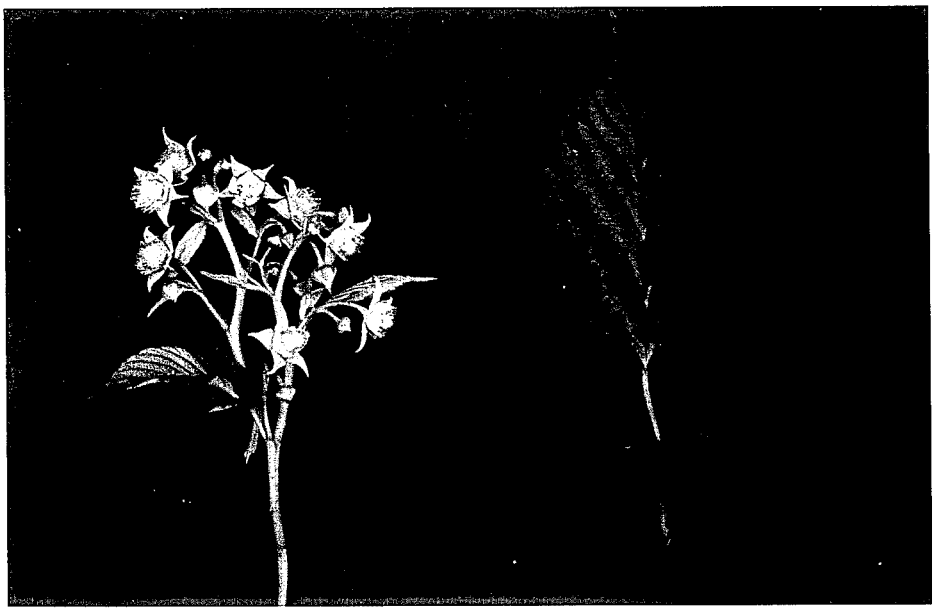
Figure 3:
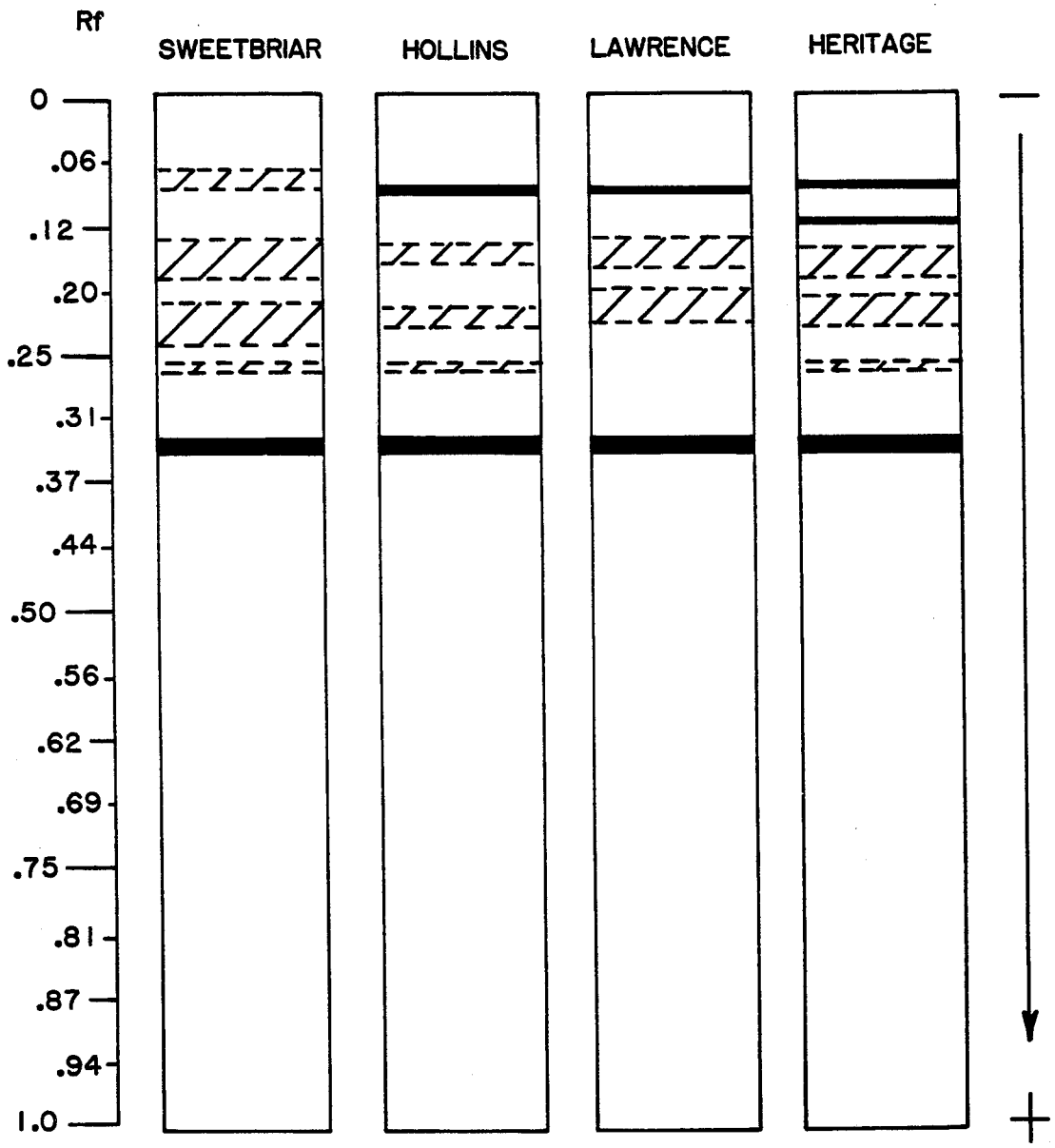
FIGS. 3, 4, 5 and 6 illustrate the isozyme separation and banding patterns of Sweetbriar, Heritage, Lawrence and Hollins raspberry varieties after polyacrylamide gel electrophoresis.
Figure 4:
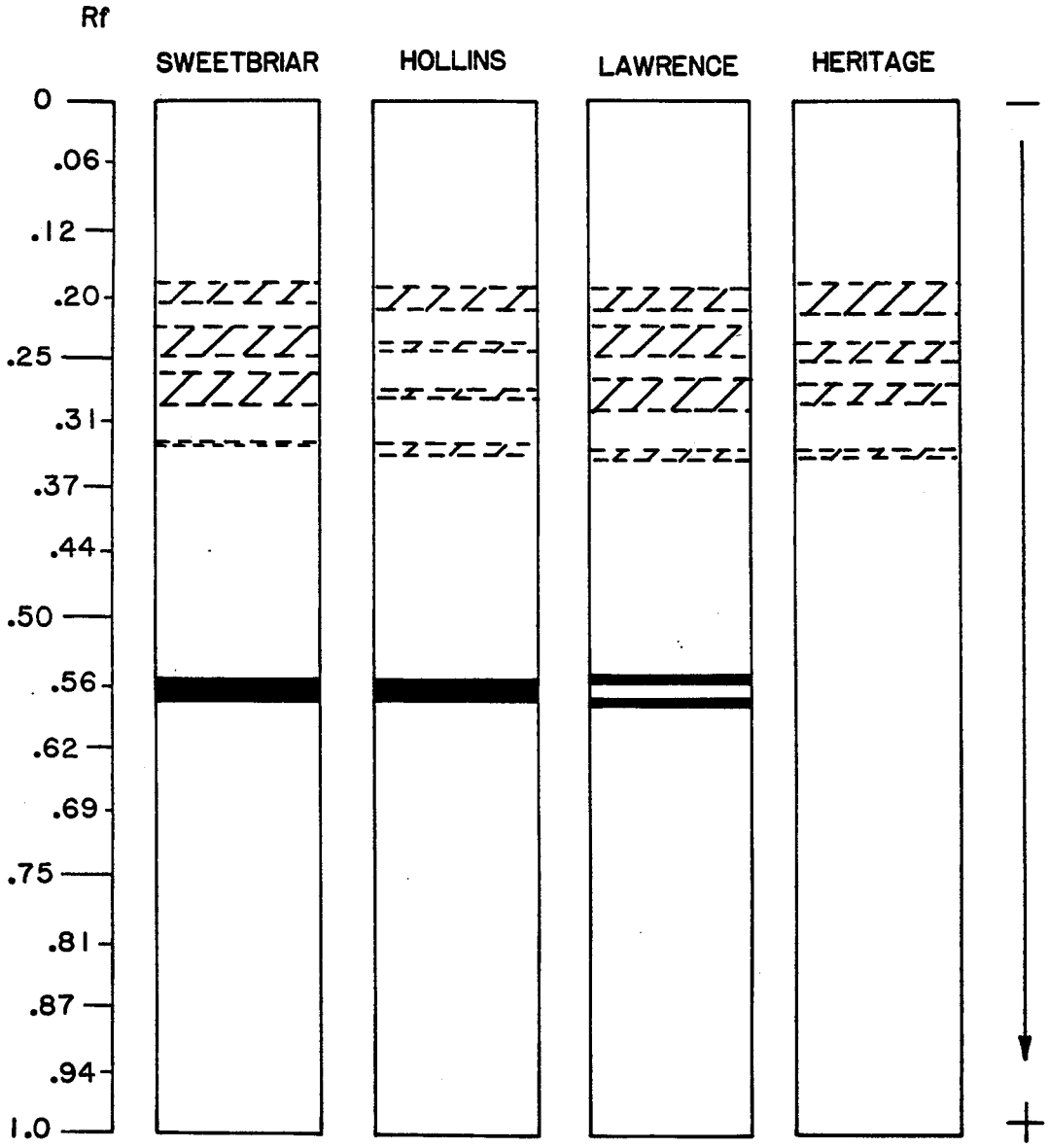
Figure 5:
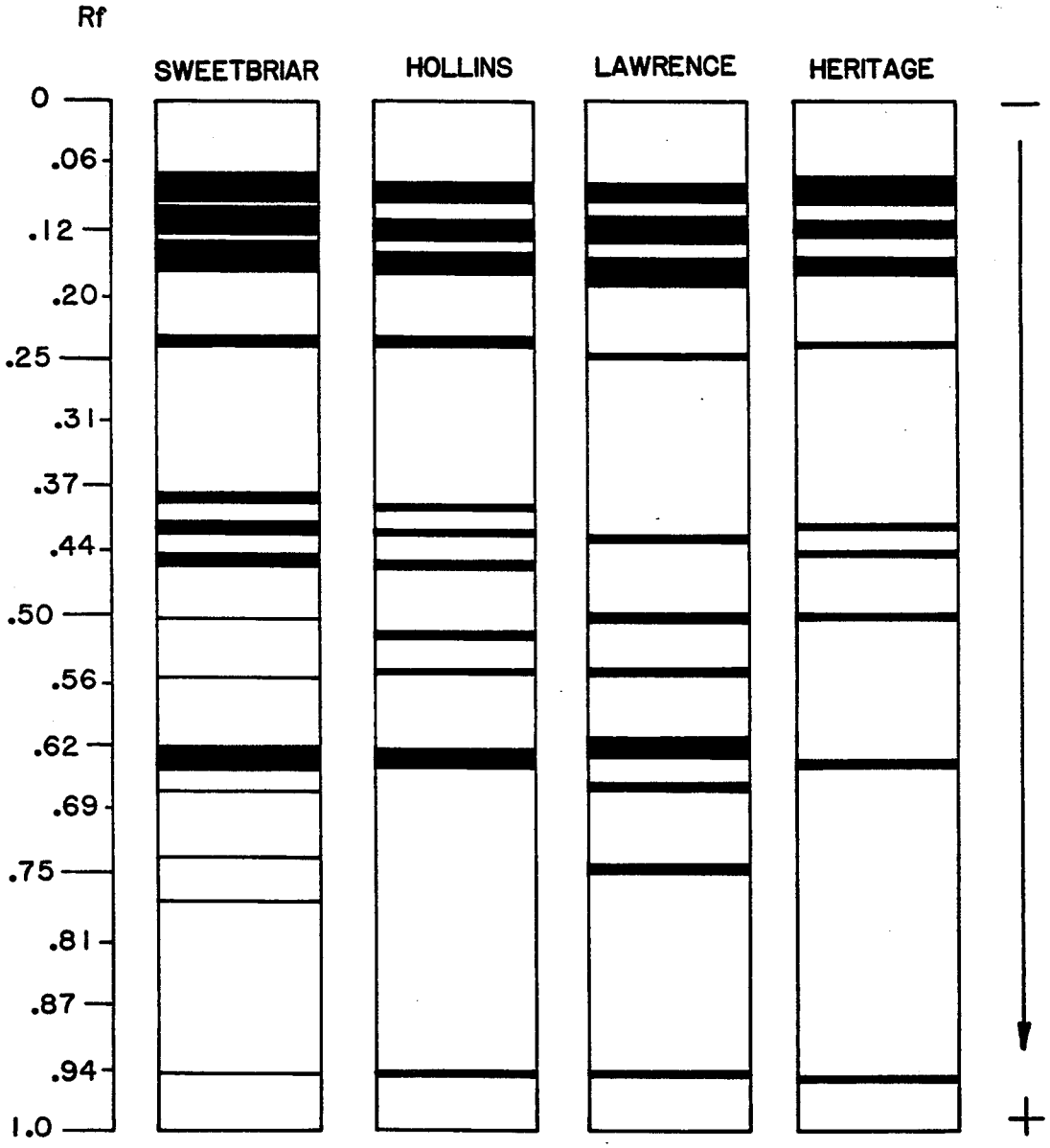
Figure 6:
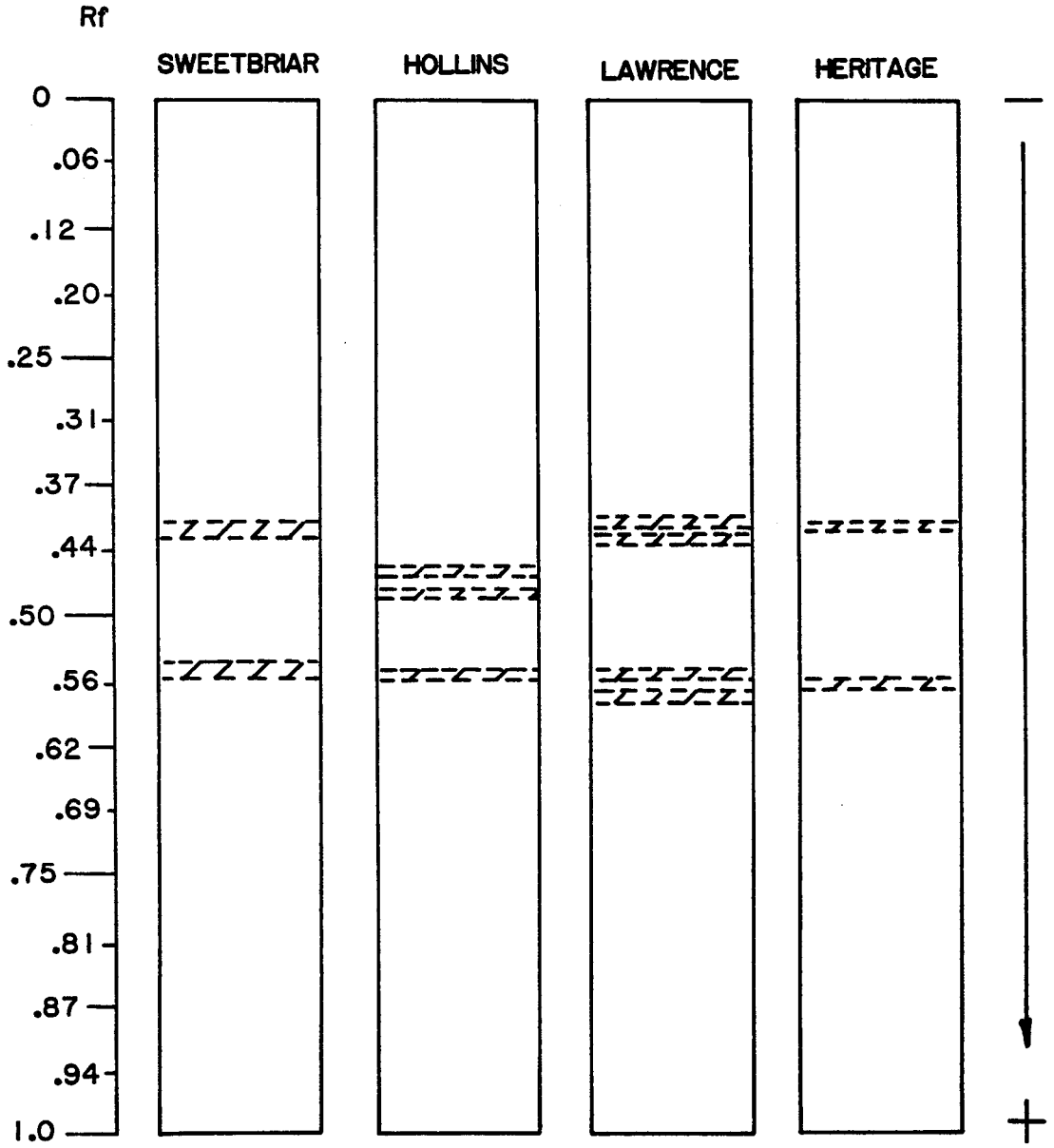
Figure 7:
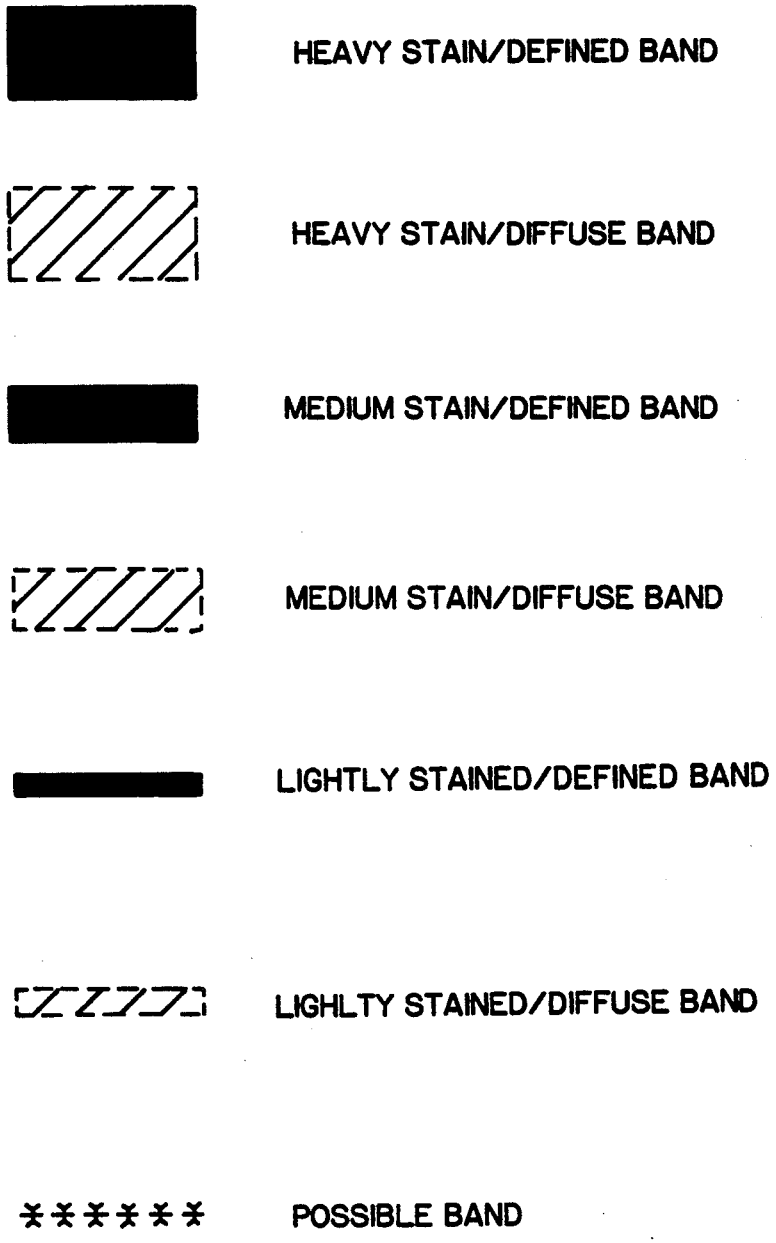
FIG. 7 is the legend for the banding patterns shown in FIGS. 3–6, inclusive.

Throughout this specification, color names beginning with a small letter signify that the name of that color as used in common speech is aptly descriptive. Color names beginning with a capital letter designate values based on The R.H.S. Colour Chart published by The Royal Horticultural Society of London, England.

The descriptive matter which follows pertains to raspberries grown in Watsonville, Calif. in 1989 and 1990, and is believed to apply to similar conditions of soil and climate elsewhere.

PLANT

The plant is vigorous, has dense deciduous foliage, and is of erect habit. It is self fruitful and productive. The fruit is adapted for the fresh dessert and culinary markets. The hardiness of the plant has not been tested. The primocane always fruits and from 20% to 30% of the cane length of the primocanes flower the year of planting.

CANES

A few (i.e., from 2 to 6) young shoots or primocanes are produced on the crown per growing season. Anthocyanin coloration is absent in leaves of very young shoots. Prior to dormancy the primocanes reach maximum size and are of long (about 60" to 72") length. Dormant canes have a diameter of about 0.44" to 0.9" at the crown and about 0.3 to 0.5" in the central third of the cane. In cross-section the canes have weak depressions—a somewhat pentagonal shape. Strong anthocyanin coloration (about Red-Purple 59B) is present on exposed young canes. Upwardly extending side shoots are present on the upper third of the canes.

Young primocane shoots are Green 144B in color, and mature and dormant primocane shoots are Green 144A in color. A medium number of soft textured small (0.8 mm to 1.5 mm in length) pigmented spines are present on the young shoots. In the central third of young shoots the spines are of medium density. The spine tips are positioned in a horizontal attitude relative to the cane axis. Spines are also uniformly distributed on the petioles. Pubescence is absent on the canes. Internodes are of medium length, averaging about 2.4" between nodes. Lenticles are not visually detectable.

On the floricanes, the laterals shoots are about 24" to 44" in length, and Yellow-Green 146D in color. There are a medium number of lateral shoots per cane (between about 15 to 27). In the mid cane area, the shoots have an average of about 11 nodes per lateral. The average number of flowers in the mid-cane area (e.g. 4th node from apex) is about 4 per node.

LEAVES

The leaves are compound. Relief between veins is medium. There are from 3 to 5 leaflets but usually 3 leaflets per leaf. The lateral leaflets overlap the terminal leaflet. Lateral leaflets are opposite. The rachis length between pairs of lateral leaflets is between about 1.3" to 2". For the terminal leaflet of a 3 leaflet leaf, the average length is about 5½" to 6" and an average width of about 5" to 6".

For a 3 leaflet leaf, the lateral leaflets have an average length of about 4¾" to 5½" and 3" to 4" in width.

Mature leaves are Yellow Green 147A on the face and Greyed Green 191A on the underside. The face of the leaves is weakly glossy. In shape the basal leaflets are ovate and often with obliqueness to leaflet halves and the terminal leaflets are ovate to cordate with a slight obliqueness to leaflet halves. Leaf margins are serrate. Petioles average about 2½" to 3½" in length, are unpigmented and Yellow-Green 144B in color. Stipules are present and erect.

FLOWERS

In Watsonville, Calif., primocanes have a blossom period from about July 10 until the first fall frost. Floricanes blossom from April 1 until June 30. The primary color of the flower is about White 155B. The flowers have five petals in free arrangement and the petals average about 3 mm to 4 mm in width and about 6 mm to 7 mm long. Pubescence is absent on the petals. The pedicels show no anthocyanin coloration. The flowers are self-fertile and will develop fruit after self pollination.

FRUIT

The primocane fruit crop is late ripening in Watsonville, beginning to ripen about August 15, it ripens uniformly throughout the season and has a medium length harvest period (about 90 to 105 or more days). The fruit is neither glossy nor dull (i.e., neutral), about Red 43B in coloration when immature, and about Red 47B coloration both while maturing and when mature. From October to November the average berry from primocane weighs about 3.0 grams.

The floricane fruit crop is harvested from around May 15 to July 30, peaking in early to mid-June. The crop ripens uniformly throughout a medium length harvest period of about 75 days.

When immature, the floricane fruit is neither glossy nor dull (i.e., neutral) and is about 42B in color; the maturing fruit darkens to about Red 45C in color and is neither glossy nor dull. When mature and fully ripe, the fruit darkens to about Red 46A and is neither glossy nor dull.

Berries harvested from floricanes during May and June have an average floricane berry weight of from about 3.0 to 3.5 grams. The berries have, in longitudinal section, an ovate shape; the axial length is from about 1.8 to 2.1 cm and the axial diameter ranges from 1.81 to 2.1 cm.

The fruit has from about 69 to 90 small smooth and substantially uniform size drupelets per berry. The drupelets at the open end that forms the berry collar are tight fitting and form a uniformly structured ring or circlet of drupelets. The seeds are of medium hardness and of a small size—weighing on the average from 1.45 to 1.56 mg. after drying at room temperature for six days.

The mature fruit is sub-acid in flavor and has a slight aroma and mild acidity. After ripening, the unpicked fruit will remain firm for about 2 days (or more if the ambient temperature is cool). At maturity, fruit is weakly attached to the receptacle and separates easily from the receptacle. The fruit cavity is of medium size. The receptacle shape can be seen in the drawing (FIG. 1). The fruit shows average resistance to bruising when hand picked. The picked fruit has good shipping qualities.

Both foliage and fruit show high resistance to strains prevalent in the Watsonville area of powdery mildew and late leaf rust.

In addition to the foregoing biological or morphological description and to provide further means for identifying the new variety of distinguishing it from some other somewhat similar and/or related raspberry varieties, the variety has been analyzed to obtain an indication of its genetic makeup. Specifically, fruit of the Lawrence (the variety of this application), Hollins (U.S. Plant patent application Ser. No. 07/713,704 filed Jun. 11, 1991), Heritage (a well-known raspberry cultivar) and Sweetbriar (the seed parent of both Hollins and Lawrence) raspberry varieties was electrophoretically analyzed on polyacrylamide gel slabs to determine the characteristic isoenzyme separation and banding patterns of each variety with respect to Acid Phosphatase, Peroxidase, Esterase and Leucine Aminopeptidase.

The enzyme stains selected for the gel electrophoresis analysis were suggested by data presented in S. Arulsekar and D. E. Parfitt, *Isozyme Analysis Procedures for Stone Fruits, Almond, Grape, Walnut, Pistachio and Fig*, 214:928–33 (1986) and J. C. Cousineau and D. S. Donnelly, *Identification of Raspberry Cultivars by Starch Gel Electrophoresis and Isoenzyme Staining*, Acta Horticulture, 262:259–67 (1989). The results of the electrophoresis anlaysis are set forth below.

TABLE 1

| | ACID PHOSPHATASE | | | |
|---|---|---|---|---|
| Rf | SWEET-BRIAR | HOLLINS | LAWRENCE | HERITAGE |
| .075–.100 | | 1 | 1 | 1 |
| .100–.125 | | | | 1 |
| .150–.175 | 1 | | 1 | 1 |
| .175–.200 | | 1 | | |
| .225–.250 | 1 | 1 | 1 | 1 |
| .300–.325 | 1 | 1 | 1 | 1 |

TABLE 2

| | PEROXIDASE | | | |
|---|---|---|---|---|
| Rf | SWEET-BRIAR | HOLLINS | LAWRENCE | HERITAGE |
| .200–.225 | 1 | 1 | 1 | 1 |
| .225–.250 | 1 | 1 | | 1 |
| .275–.300 | 1 | 1 | 1 | 1 |

TABLE 2-continued

| | PEROXIDASE | | | |
|---|---|---|---|---|
| Rf | SWEET-BRIAR | HOLLINS | LAWRENCE | HERITAGE |
| .575–.600 | | | 1 | |
| .625–.650 | 1 | 1 | 1 | |

TABLE 3

| | ESTERASE | | | |
|---|---|---|---|---|
| Rf | SWEET-BRIAR | HOLLINS | LAWRENCE | HERITAGE |
| .075–.100 | 1 | 1 | 1 | 1 |
| .100–.125 | 1 | 1 | 1 | 1 |
| .150–.175 | 1 | 1 | 1 | 1 |
| .200–.225 | | 1 | | |
| .225–.250 | 1 | | 1 | 1 |
| .375–.400 | 1 | 1 | | |
| .400–.425 | 1 | 1 | 1 | 1 |
| .425–.450 | 1 | | | 1 |
| .450–.475 | | 1 | | |
| .475–.500 | 1 | | 1 | 1 |
| .500–.525 | | 1 | | |
| .525–.550 | | | 1 | |
| .550–.575 | 1 | 1 | | |
| .625–.650 | 1 | | 1 | |
| .650–.675 | 1 | 1 | | 1 |
| .675–.700 | | | 1 | |
| .725–.750 | 1 | | | |

TABLE 3-continued

| | ESTERASE | | | |
|---|---|---|---|---|
| Rf | SWEET-BRIAR | HOLLINS | LAWRENCE | HERITAGE |
| .750–.775 | | | 1 | |
| .775–.800 | 1 | | | |
| .925–.950 | 1 | 1 | 1 | 1 |

TABLE 4

| | LEUCINE AMINOPEPTIDASE | | | |
|---|---|---|---|---|
| Rf | SWEET-BRIAR | HOLLINS | LAWRENCE | HERITAGE |
| .400–.425 | 1 | | 1–2 | 1 |
| .475–.500 | | 2 | | |
| .525–.550 | 1 | 1 | 2 | 1 |

In the analysis of the enzymatic comparisons with Sweetbriar and Heritage, the Lawrence variety displays a significant difference in the banding patterns of Peroxidase and Esterase. Bands appear in the electrophoretic analysis of the Lawrence variety which do not appear in the electrophoretic analysis of Sweetbriar and Heritage. In addition, the Lawrence variety displays a significant difference in the banding patterns of Peroxidase, Esterase and Leucine Aminopeptidase from Hollins, a related variety of raspberry.

I claim:

1. A new vareity of raspberry cv. "Lawrence" as herein illustrated and described.

* * * * *